(12) United States Patent
Shang et al.

(10) Patent No.: US 12,163,574 B2
(45) Date of Patent: Dec. 10, 2024

(54) MOTOR MODULE

(71) Applicant: Precision Robotics Limited, London (GB)

(72) Inventors: Jianzhong Shang, Dartford (GB); Etienne Francois Joseph Dondez, London (GB); Tamas Csaba Hernadi, London (GB); Michele Camerlengo, London (GB)

(73) Assignee: Precision Robotics Limited, London (GB)

( * ) Notice: Subject to any disclaimer, the term of this patent is extended or adjusted under 35 U.S.C. 154(b) by 48 days.

(21) Appl. No.: 18/023,159

(22) PCT Filed: Aug. 13, 2021

(86) PCT No.: PCT/GB2021/052105
§ 371 (c)(1),
(2) Date: Feb. 24, 2023

(87) PCT Pub. No.: WO2022/043657
PCT Pub. Date: Mar. 3, 2022

(65) Prior Publication Data
US 2023/0349451 A1 Nov. 2, 2023

(30) Foreign Application Priority Data

Aug. 24, 2020 (GB) ..................... 2013192

(51) Int. Cl.
*F16H 19/04* (2006.01)
*B25J 9/10* (2006.01)
(Continued)

(52) U.S. Cl.
CPC ............ *F16H 19/04* (2013.01); *B25J 9/1035* (2013.01); *H02K 7/116* (2013.01); *A61B 34/30* (2016.02); *H02K 2213/06* (2013.01)

(58) Field of Classification Search
CPC .................... F16H 19/04; A61B 34/30; A61B 2017/2923; A61B 2017/2943
See application file for complete search history.

(56) References Cited

U.S. PATENT DOCUMENTS 3,593,712 A * 7/1971 Weaver ............. A61M 15/0085
261/DIG. 65
6,458,121 B1 * 10/2002 Rosenstock .............. A61N 1/40
606/41

(Continued)

FOREIGN PATENT DOCUMENTS

| CN | 208511177 U | 2/2019 | |
|---|---|---|---|
| JP | 2020501822 A * | 1/2020 | ........... A61B 17/068 |
| WO | 2019191420 A1 | 10/2019 | |

OTHER PUBLICATIONS

International Search Report from PCT International Application No. PCT/GB2021/052105, dated Nov. 26, 2021.

*Primary Examiner* — Bobby Rushing, Jr.
(74) *Attorney, Agent, or Firm* — KILPATRICK TOWNSEND & STOCKTON LLP

(57) ABSTRACT

A motor module comprising a primary pinion rotatably driveable by a primary motor, a first primary rack moveably engageable with the primary pinion and a second primary rack moveably engageable with the primary pinion. Rotation of the primary pinion causes movement of the first primary rack in a first direction, and movement of the second primary rack in a second direction, whereby the first and second primary racks and the primary pinion together form an antagonistic rack and pinion mechanism.

13 Claims, 12 Drawing Sheets

(51) Int. Cl.
  *H02K 7/116*   (2006.01)
  *A61B 34/30*   (2016.01)

(56) References Cited

U.S. PATENT DOCUMENTS

| | | | |
|---|---|---|---|
| 2013/0172906 A1* | 7/2013 | Olson | A61B 34/30 |
| | | | 606/130 |
| 2014/0187889 A1* | 7/2014 | Cohen | A61B 5/0015 |
| | | | 600/365 |
| 2014/0276761 A1 | 9/2014 | Parihar et al. | |
| 2015/0173840 A1 | 6/2015 | Lohmeier | |
| 2015/0265355 A1 | 9/2015 | Prestel et al. | |
| 2017/0156711 A1 | 6/2017 | Jogasaki et al. | |
| 2020/0078104 A1* | 3/2020 | Bailey | A61B 34/35 |

* cited by examiner

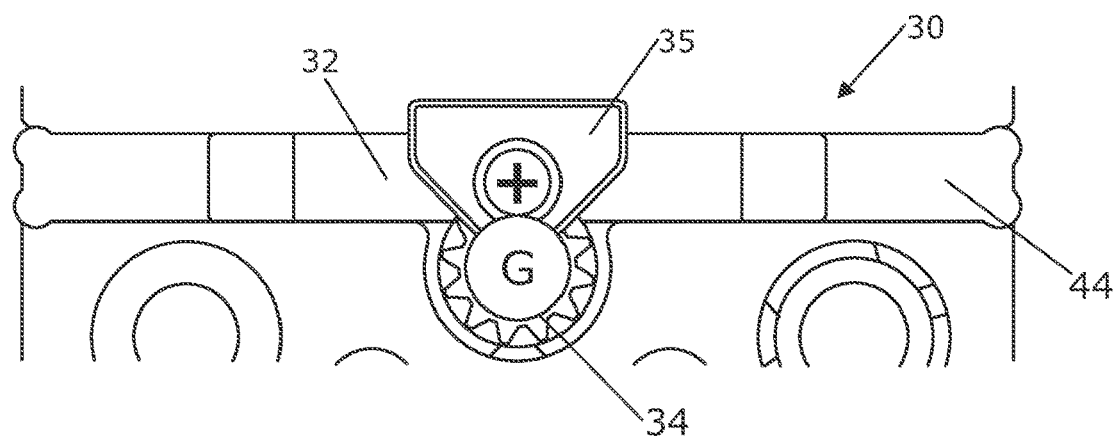
Figure 7
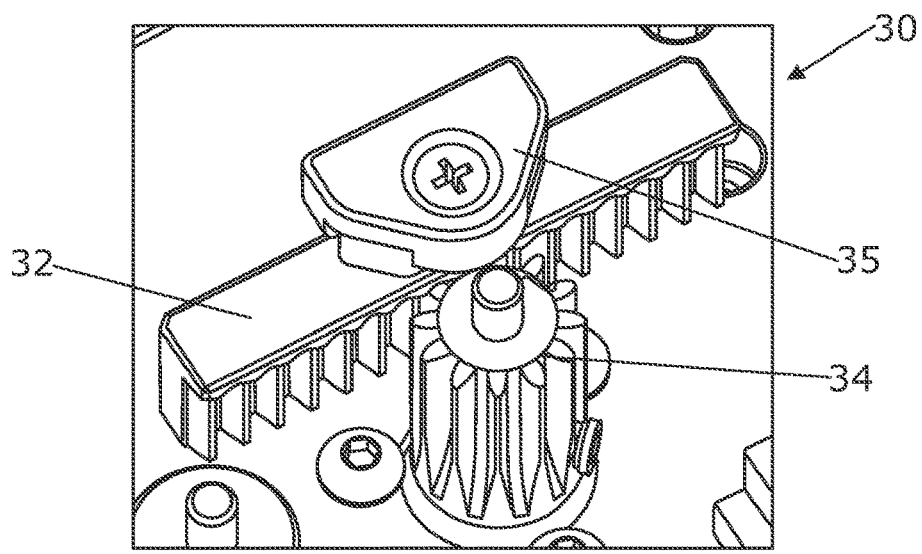
Figure 8
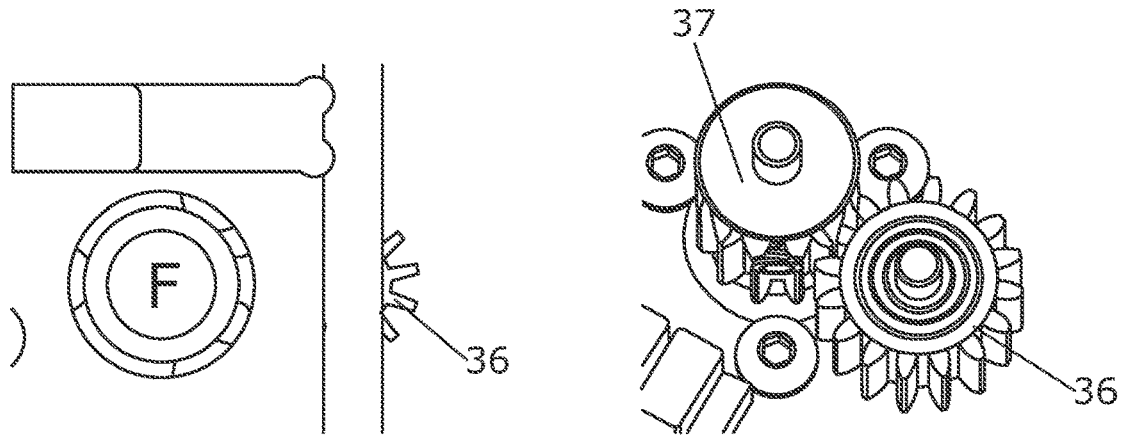
Figure 9
Figure 10

MOTOR MODULE

CROSS-REFERENCE TO RELATED APPLICATIONS

This Application is a National Stage Application under 35 U.S.C. § 371 of PCT Application No. PCT/GB2021/052105, filed Aug. 13, 2021, which claims priority to UK Patent Application No. 2013192.6, filed Aug. 24, 2020, the entire contents of which are incorporated by reference herein.

BACKGROUND OF THE INVENTION

1. Field of the Invention

This invention relates to a motor module, and particularly, although not exclusively, to a motor module for use in the field of surgical robotics and configured to actuate a surgical instrument.

2. Description of the Related Art

Robotic systems are increasingly being used to carry out surgical procedures, particularly minimally invasive surgical procedures, in which miniaturised surgical instruments may be remotely controlled by a surgeon to perform the various actions required of the procedure.

Known surgical instruments, forming part of robotic surgical systems, comprise a shaft, an articulation portion and an end effector. The shaft may extend from other components of the surgical robot which control and drive movement of the articulation portion and the end effector. The shaft may thereby facilitate positioning of the articulation portion and end effector at the required area of the patient. The articulation portion may comprise a plurality of joints positioned adjacent to one another to provide degrees of freedom of movement to the end effector relative to the shaft. Lastly, the end effector may be adapted to carry out particular actions required in surgical procedures. For example, the end effector may provide forceps or a scalpel.

Known end effectors, articulation portions, shafts and combinations thereof are small in their maximum width or diameter, less than 1 cm for example. However, these portions of known surgical instruments, and particularly the shaft, may extend over lengths considerably larger than the maximum width. The narrow width and extended length of the surgical instrument enable surgical techniques to be performed as minimally invasive procedures. Additionally known surgical instruments are manufactured to be disposable or single-use products to ensure their sterility when used for a surgical procedure.

In order to provide articulation portions and end effectors of the required dimensions, known surgical instruments are driven by tendons wherein a first end of a tendon is attached to a particular joint or portion of an end effector, the tendon extends along a lumen of the shaft and a second end of the tendon is mechanically coupled to a motor. The motor may actuate the tendon which in turn actuates the joint or end effector it is attached to.

In order to actuate a plurality of joints, a plurality of tendons may be required. In turn, several motors may be required to actuate the tendons.

Known robot surgical systems comprise a motor module configured to provide all the motors required to actuate a surgical instrument. Such motor modules may be expensive to produce due to the electrical components involved and therefore manufactured to be used repeatedly in several surgical procedures.

Known motor modules may be mechanically couplable to a surgical instrument via a driver module configured to receive actuation inputs from the motor module and transfer those actuations to the tendons of the surgical instrument.

However, known modules provide actuation inputs as rotational actuations based on the rotations provided by the motors. As a result the mechanical coupling of the motor module to the drive module is complex due to the alignment of motorised actuators in the motor module with capstans in the driver module. This mechanical coupling may then be complicated further by the requirement to provide a sterile barrier between the non-sterile motor module and the sterile driver module in order to prevent contamination of the surgical instrument.

Intricate mechanical coupling of robotic parts may be challenging because medical staff tend to have expertise is in the field of medicine rather than robotics. The use of known surgical robots may therefore be frustrating and/or overly time consuming for the medical staff involved.

SUMMARY OF THE INVENTION

According to an aspect of the invention there is provided a motor module comprising: a primary pinion rotatably driveable by a primary motor, a first primary rack moveably engageable with the primary pinion and a second primary rack moveably engageable with the primary pinion; wherein rotation of the primary pinion causes movement of the first primary rack in a first direction, and movement of the second primary rack in a second direction, whereby the first and second primary racks and the primary pinion together form an antagonistic rack and pinion mechanism.

Each primary rack may moveably engage with the primary pinion by any suitable means. For example the primary pinion may comprise a plurality of teeth extending from its circumference and each primary rack may comprise a plurality of teeth extending from a side of the primary rack proximate to the primary pinion wherein the teeth of the primary pinion are adapted to interlock with the teeth of each primary rack. When, in use, the primary pinion is caused to rotate by the primary motor, angular movement of the primary pinion's teeth may produce a force on the teeth of the primary rack and thereby cause the primary rack to move translationally relative to the primary pinion.

In another embodiment, the circumference of the primary pinion and the side of each primary rack proximate to the primary pinion may comprise a material with a high coefficient of friction and each primary rack may be positioned relative to the primary pinion such that the high friction materials are in contact with one another. When, in use, the primary pinion is caused to rotate by the primary motor, angular movement of the primary pinion's high friction circumferential surface may produce a force on the high friction surface of the primary rack and thereby cause the primary rack to move translationally relative to the primary pinion.

The first primary rack may be positioned along a first tangent to the primary pinion and the second primary rack may be positioned along a second tangent to the primary pinion different to the first tangent. Accordingly, rotation of the primary pinion may cause the first and second primary racks to move in different directions, for example along the different tangential lines.

Further, the position of the first and second tangents, relative to the primary pinion, may be substantially opposite to one another. Therefore, rotation of the primary pinion in a rotational direction (i.e. clockwise or anticlockwise) may cause the direction of movement of the first primary rack (the first direction) to be substantially opposite to the direction of movement of the second primary rack (the second direction). In other words, the first and second primary racks are caused to move antagonistically to one another as part of an antagonistic rack and pinion mechanism.

By means of the invention a motor module is provided comprising a rack and pinion mechanism that converts a rotational movement provided by a motor to translational movement of first and second racks, thus obviating the need to convert rotational movement to translational movement of tendons within a driver module.

The driver module may thus be simplified, and its cost of manufacture reduced. This is advantageous if the driver module is to be disposable, which may be desirable if the motor module is to be used in a sterile environment.

Such a motor module also obviates the need to transfer actuation from the motor module to a driver module as rotational movement, which may require intricate alignment of small components. Rather, actuation may be transferred from the motor module to the driver module as a translational movement wherein simple alignment of the entire motor module with the entire driver module may provide sufficient alignment of components forming part of each of the motor and driver modules to facilitate actuation being transferred from one to the other.

Additionally, the provision of an antagonistic rack and pinion mechanism, with first and second primary racks that move antagonistically to one another, facilitates actuation of a pair of antagonistic tendons. For example, in order to actuate a joint of a surgical instrument in a first direction a first tendon may be actuated (pulled), and to actuate the joint in a second direction, a second, antagonistic, tendon may be actuated (pulled). An antagonistic rack and pinion mechanism according to the invention may actuate the first tendon through rotation of the primary pinion in a first direction, and the second tendon through rotation of the primary pinion in a second, opposite, direction.

In embodiments of the invention the motor module may comprise a plurality of motors and a plurality of antagonistic rack and pinion mechanisms wherein the primary pinion of each antagonistic rack and pinion mechanism is driveable by a respective one of the motors.

In such embodiments of the invention the motor module may actuate a plurality of tendons and thereby actuate the various joints and end effectors that form a surgical instrument. Further each motor and associated antagonistic rack and pinion mechanism may actuate a respective pair of antagonistic tendons.

In embodiments of the invention at least one of the antagonistic rack and pinion mechanisms may be a dual antagonistic rack and pinion mechanism further comprising: a third primary rack moveably engageable with the primary pinion and a fourth primary rack moveably engageable with the primary pinion; wherein rotation of the primary pinion causes movement of the third primary rack in the first direction and movement of the fourth primary rack in the second direction.

In such embodiments of the invention four primary racks may be moved by the same primary pinion and hence the same motor. Particularly, the primary pinion may cause the first and third racks to move in the same direction as one another and the second and fourth racks move in the same direction as one another as well as substantially opposite to the direction of the first and third racks. Hence two pairs of antagonistic actuations may be provided.

This may be particularly advantageous for providing actuation of a surgical instrument comprising two adjacent joints that are rotatable in the same directions. For example, if each joint is able to provide up to ±45° of rotation, two joints adjacent to one another may combine to provide up to ±90° of rotation.

A dual antagonistic rack and pinion mechanism may provide simultaneous actuation of the antagonistic pair of tendons associated with each of the adjacent joints. In other words, the dual antagonistic rack and pinion mechanism may be used to actuate both adjacent joints simultaneously. This allows the two adjacent joints to actuate complimentarily with one another and avoids a situation where their actuations contradict one another and cancel each other out. Further, the actuation of both joints may be driven by a single motor only, thereby reducing the complexity, size and cost of the motor module.

In embodiments of the invention the primary pinion of the or each dual antagonistic rack and pinion mechanism may comprise a first portion and a second portion, the first and second primary racks being engageable with the first portion of the primary pinion, and the third and fourth primary racks being engageable with the second portion of the primary pinion.

In such embodiments of the invention the first and second portions of the primary pinion may have different radii and may thereby cause the first and second primary racks to move with a different gearing ratio to the third and fourth primary racks. For example, if the second portion has a larger radius than the first portion then a rotation of the primary pinion may cause the third and fourth primary racks to move a greater distance than the first and second primary racks in their respective directions.

The radii of the first and second portions may be configured to ensure that two adjacent joints of a surgical instrument are each actuated to rotate through the same angle of rotation despite a larger tendon actuation being required for the more distal of the two joints.

In embodiments of the invention each primary rack may further comprise an actuation portion, the motor module may further comprise an interface plate comprising a plurality of first apertures and a plurality of second apertures, the actuation portion of each first primary rack, or each first and third primary rack, may be moveable within a respective first aperture, and the actuation portion of each second primary rack, or of each second and fourth primary rack, may be moveable within a respective second aperture.

In such embodiments of the invention the interface plate may cover and protect internal components of the motor module, such as the motor(s) and primary pinion(s). Further, the interface plate maybe engageable with a driver module, or a sterile barrier that is in turn engageable with a driver module.

However, in order to actuate actuators forming part of the driver module (which in turn actuate the tendons of the surgical instrument), the interface plate comprises apertures through which the actuation portions of the primary racks may interact with the actuators of the driver module (or intermediary actuators of the sterile barrier).

In embodiments of the invention each primary rack may be movable linearly.

In such embodiments of the invention the motor module may comprise a linear channel associated with each first and second primary rack wherein the respective primary rack is movably receivable within the linear channel but is restricted to moving linearly between a first end and a second end of the linear channel only.

In such embodiments of the invention which also comprise one or more dual antagonistic rack and pinion mechanisms, each third and fourth primary rack may be movably receivable in the same linear channel as the associated first or second primary rack or may be movably receivable in a separate linear channel to the associated first or second primary rack. Regardless, each third and fourth primary rack may be restricted to moving only linearly between a first end and a second end of the linear channel it is received by.

Converting the rotational movement provided by the motors to linear movement may be particularly advantageous as tendons used for actuating a surgical instrument may ideally be actuated linearly, parallel to the shaft of the surgical instrument. Further, the linear channels and resulting linear movement of the primary racks may be configured to be parallel to the axis of the surgical instrument shaft, thereby avoiding the need to significantly alter the direction of the tendons as they exit the shaft with Bowden cables or pulleys.

In embodiments of the invention the motor module may further comprise a secondary motor and a secondary rack and pinion mechanism, the secondary rack and pinion mechanism comprising: a secondary pinion rotatably driveable by the secondary motor, a secondary rack movably engageable with the secondary pinion wherein rotation of the pinion causes movement of the secondary rack.

In such embodiments of the invention the second rack and pinion mechanism may convert rotational movement of the secondary motor to a single translational, and optionally linear, movement of one secondary rack. The secondary rack and pinion mechanism may be for actuating a tendon which works independently (rather than antagonistically), or for a different form of actuation of the surgical instrument such as providing rotation of the shaft of the surgical instrument.

The secondary rack may be positioned along a tangent to the secondary pinion moveably engage with the secondary pinion by any suitable means. For example the secondary pinion may comprise a plurality of teeth extending from its circumference and the secondary rack may comprise a plurality of teeth extending from a side of the secondary rack proximate to the secondary pinion wherein the teeth of the secondary pinion are adapted to interlock with the teeth of the secondary rack. In another example the circumference of the secondary pinion and the side of the secondary rack proximate to the secondary pinion may comprise a material with a high coefficient of friction and the secondary rack may be positioned relative to the secondary pinion such that the high friction materials are in contact with one another.

In embodiments of the invention the motor module may comprise any suitable number of secondary motors and secondary rack and pinion mechanisms.

In embodiments of the invention the motor module is removably mountable to a mounting bracket and is movable along the mounting bracket.

In such embodiments of the invention a sterile barrier and a driver module with associated surgical instrument may also be removably mountable to the mounting bracket. The mounting bracket may be adapted for positioning the surgical instrument in the required position relative to the patient. For example, the mounting bracket may be coupled to a first end of a manipulator arm, a second end of which may be mountable to a surface (such as the floor or the operating table). The manipulator arm may provide a plurality of degrees of freedom to allow the mounting bracket to be selectively positioned to allow the surgical instrument the required access to the patient.

The motor module, and the driver module, may be movable along the mounting bracket to provide a degree of freedom between the motor module (and driver module) and the patient. For example, this may allow surgical instrument to be moved towards and away from the patient.

In embodiments of the invention a plurality of motor modules may be removably mountable to the mounting bracket at the same time to allow a plurality of surgical instruments to be positioned together and used together for a surgical procedure.

In embodiments of the invention the mounting bracket may comprise a translation rack and the motor module may further comprise a translation motor and a translation pinion rotatably driveable by the translation motor and engageable with the translation rack when the motor module is mounted to the mounting bracket such that rotation of the translation pinion causes movement of the motor module relative to the mounting bracket.

In such embodiments of the invention the translation pinion may be moveably engageable with the translation rack wherein rotation of the translation pinion causes the translation pinion to roll along the translation rack. The combination of the translation pinion and translation rack may provide conversion of rotational movement of the translation motor to a translational, and optionally linear, movement of the motor module relative to the mounting bracket.

The translation rack and translation pinion may each be positioned such that, when the motor module is mounted to the mounting bracket, the translation rack is positioned along a tangent to the translation pinion.

The translation pinon may be engageable with the translation rack by any suitable means. For example the translation pinion may comprise a plurality of teeth extending from its circumference and the translation rack may comprise a plurality of teeth extending from a side of the translation rack proximate to the translation pinion (when the motor module is mounted to the mounting bracket) wherein the teeth of the translation pinion are adapted to interlock with the teeth of the translation rack. In another example the circumference of the translation pinion and the side of the translation rack proximate to the translation pinion (when the motor module is mounted to the mounting bracket) may comprise a material with a high coefficient of friction and the translational rack may be positioned relative to the translational pinion such that the high friction materials are in contact with one another.

In embodiments of the invention the motor module may comprise any suitable number of translation motors and translation pinions and the mounting bracket may comprise any suitable number of translation racks.

In embodiments of the invention the motor module may further comprise a gear arrangement rotatably driveable by the translation motor and rotatably and mechanically coupled to the translation pinion such that the translation pinion is rotatably driven by the translation motor via the gear arrangement.

In such embodiments of the invention the gear arrangement may be adapted to provide rotation of the translational pinion about a different axis to the translational motor. This may be advantageous as it may allow the translational pinion to be positioned proximate to an edge or side of the motor module so that a portion of the translational pinion can extent outwardly from the motor module in order to engage with the translational rack when the motor module is mounted to the mounting bracket. Meanwhile, the translational motor may be positioned more centrally within the motor module so that it may be covered and protected by the casing of the motor module.

Also, the gear arrangement may be adapted to provide gearing of the translation pinion's rotation relative to the rotation generated by the translational motor. For example, the translation pinion could be geared to rotate with a greater angular velocity than the translational motor to provide the resulting translation of the motor module with greater responsiveness relative to the input provided by the motor. Alternatively, the translation pinion could be geared to rotate with a lower angular velocity than the translational motor to provide the translational movements that may be achieved by motor module with greater precision.

In embodiments of the invention the motor module may be configured to actuate a surgical instrument. Additionally, the motor module may further comprise an instrument mount mechanically couplable to a surgical instrument such that the surgical instrument is removably mountable to the motor module.

In such embodiments of the invention the surgical instrument may be directly mountable to the motor module or mountable to the motor module via a driver module and/or a sterile barrier.

The instrument mount may comprise a means for facilitating slidable engagement of the surgical instrument (directly or indirectly) to the motor module such as channels, grooves or ridges configured to slidably engage with corresponding channels groove or ridge forming part of the surgical instrument, or associated driver module or sterile barrier.

Also, the instrument mount may comprise a means for facilitating lockable engagement of the surgical instrument (directly or indirectly) to the motor module such as a latch configured to lockably engage with a corresponding recess forming part of the surgical instrument, or associated driver module or sterile barrier. Alternatively, the means for facilitating lockable engagement of the surgical instrument (directly or indirectly) may be a recess for receiving a latch forming part of the surgical instrument, or associated driver module or sterile barrier.

However, in embodiments of the invention the motor module may be configured to actuate other instruments. For example, the motor module may form part of a robotic system configured for manufacturing processes, bomb disposal or performing other tasks in environments that are too small or inhospitable for humans.

In embodiments of the invention the motor module comprises a processor electrically connectable to at least one motor.

In such embodiments of the invention the processor may receive control signals from a control module forming part of the robotic surgical system. Based on the control signals the processor may selectively provide electrical power to the or each motor forming part of the motor module in order to cause the motor to provide a rotational movement.

In some embodiments of the invention the processor may be mounted to a motherboard and may be electrically connectable to at least one motor via the motherboard.

In some embodiments of the invention the motor module may comprise any suitable number of processors. For example, the motor module may comprise a processor to control each motor or the motor module may comprise a processor to control each type of motor (i.e. a processor to control all primary motors, a processor to control all secondary motors and a motor to control all translational motors).

In embodiments of the invention the motor module may comprise a safety watchdog electrically connectable to the processor.

In such embodiments of the invention the safety watchdog may monitor motor module for errors such as a failed motor, a motor that is unable to complete its controlled movement (which may indicate a blockage within the system) or the processor failing to carry out a control signal.

In some embodiments of the invention the safety watchdog may be mounted to a motherboard and may be electrically connectable to the or each processor via the motherboard. The safety watchdog may also be electrically connectable to one or more motors via the motherboard.

In embodiments of the invention the motor module further comprises a cooling fan.

In such embodiments of the invention the cooling fan may be operated to cause air to flow through the motor module and facilitate cooling of the internal components. Further, the cooling fan may be oriented to cause air to flow parallel to the motor(s) and processor(s) to improve cooling of these components.

In embodiments of the invention the motor module further comprises a heat sink.

In such embodiments the heat sink may absorb heat produced by the processor(s), safety watchdog and/or motor(s) during use of the motor module. The heat sink may therefore help stop components of the motor module from overheating. The motor module may comprise any suitable number of heat sinks, for example a separate heat sink may accompany each processor and the safety watchdog.

Each heat sink may comprise a cooling surface with features such as channels, grooves, ridges or fins for example that increase the surface area of the heat sink and improve heat dissipation from the heat sink. Additionally, the channels, grooves, ridges or fins may extend parallel to the direction air flow caused by the cooling fan to further improve the heat dissipation from the heat sinks and the cooling of the associated components.

BRIEF DESCRIPTION OF THE DRAWINGS

The invention will now be described by way of example only with reference to the accompanying drawings in which:

FIGS. 7 and 8 are schematic representations of a secondary rack and pinion mechanism forming part of the motor module of FIG. 1;

FIGS. 9 and 10 are each schematic representations of a translation pinion forming part of the motor module of FIG. 1;

DETAILED DESCRIPTION OF THE EMBODIMENTS

Figure 1:
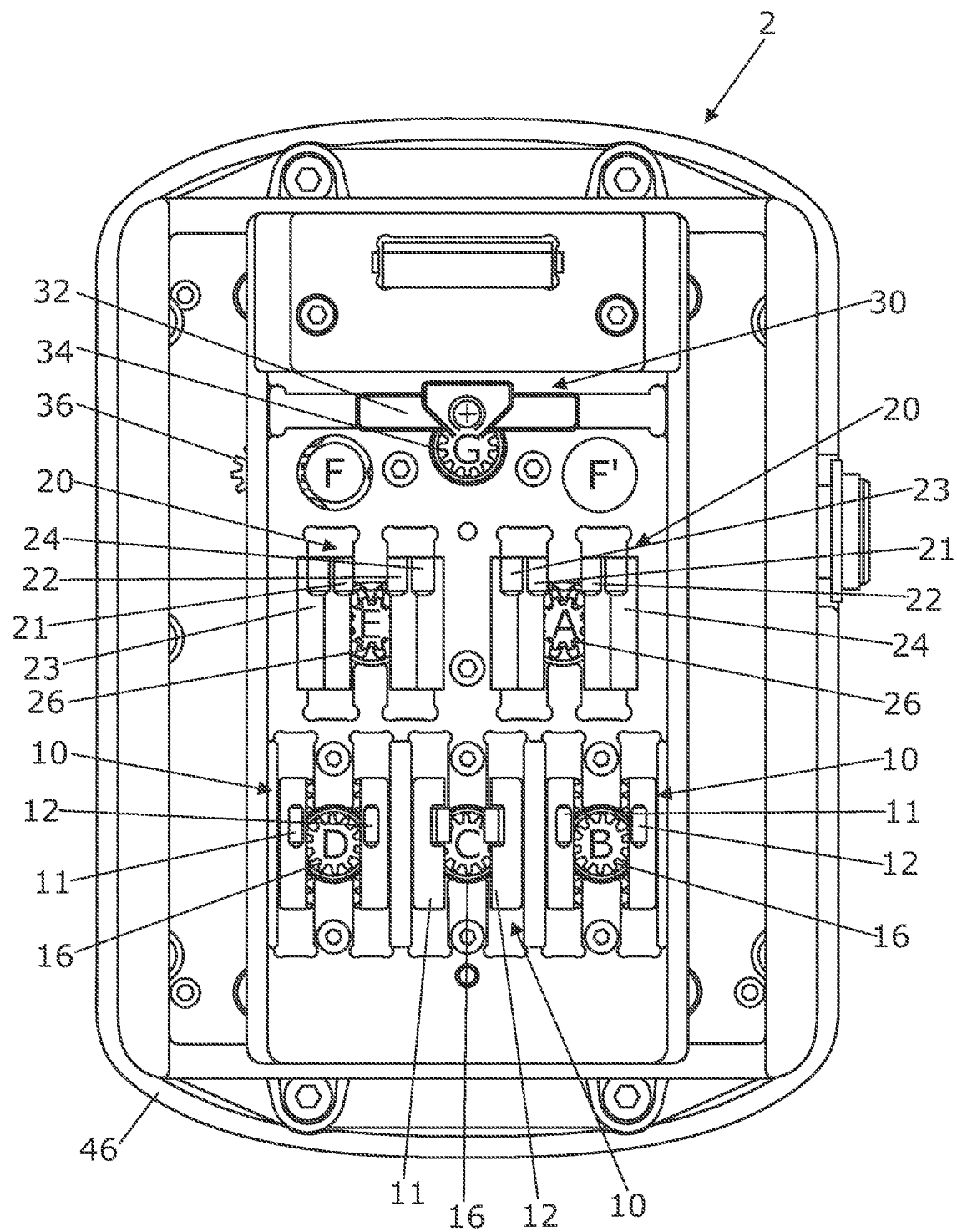
FIG. 1 is a schematic representation of a motor module according to an embodiment of the invention.

Referring initially to FIG. 1, a motor module according to an embodiment of the invention is designated generally by the reference numeral 2. The motor module 2 comprises three antagonistic rack and pinion mechanisms 10, two dual antagonistic rack and pinion mechanisms 20, a secondary rack and pinion mechanism 30 and a translation pinion 36. The motor module further comprises an outer casing 46 (shown more clearly in FIGS. 13a, 13b and 13c).

However, other embodiments of the invention may comprise either more or fewer of each of these features.

Each antagonistic rack and pinion mechanism 10 comprises a first primary rack 11, a second primary rack 12 and a primary pinion 16.

Each dual antagonistic rack and pinion mechanism 20 comprises a first primary rack 21, a second primary rack 22, a third primary rack 23, a fourth primary rack 24 and a primary pinion 26.

The secondary rack and pinion mechanism 30 comprises a secondary rack 32 and a secondary pinion 34.

The motor module 2 also comprises a plurality of motors, each of which is associated with a respective one of the antagonistic rack and pinion mechanisms 10, dual antagonistic rack and pinion mechanisms 20, secondary rack and pinion mechanism 30 and the translation pinion 36.

The location of each motor is indicated with reference signs A, B, C, D, E, F and G.

Figure 2:
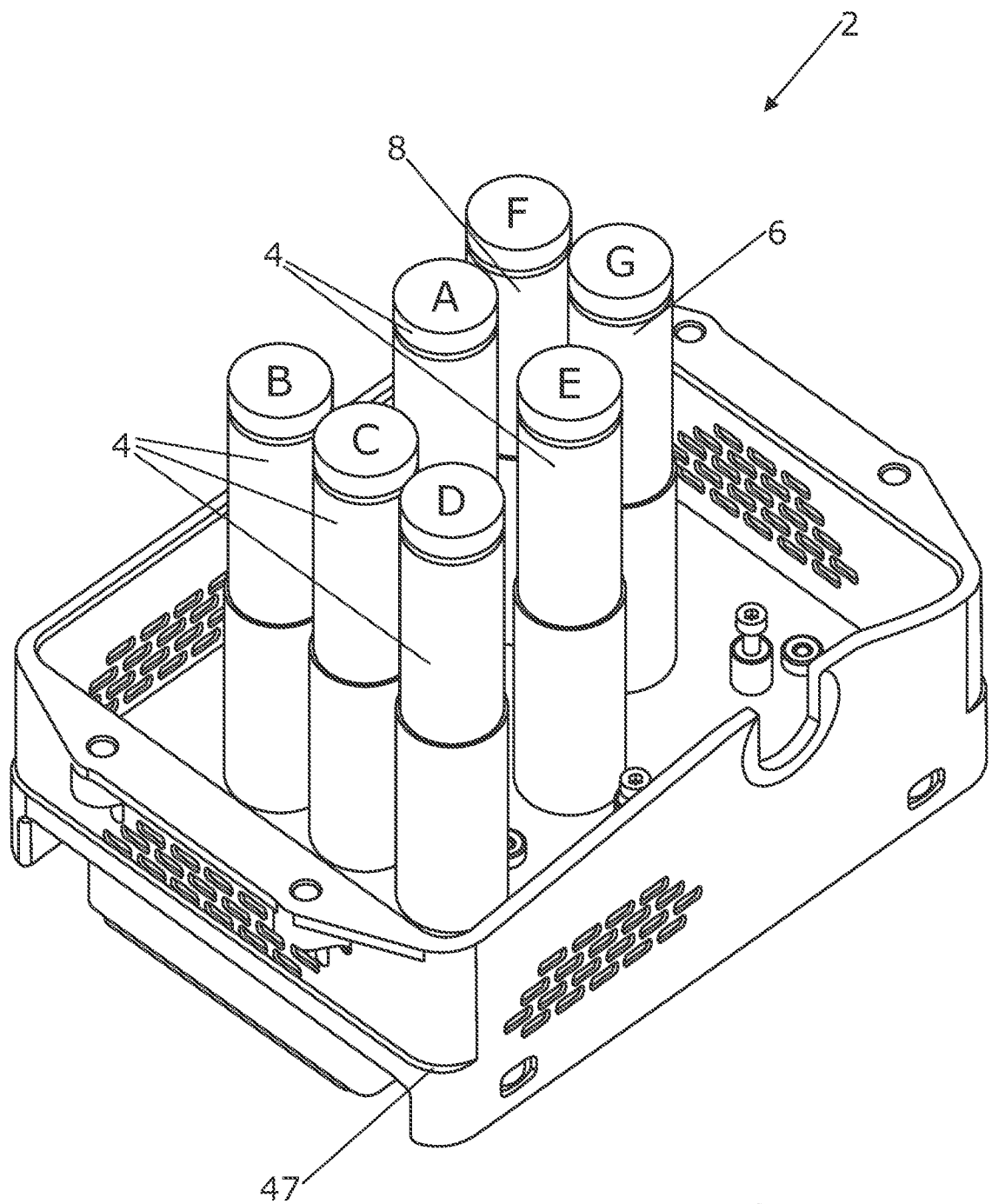
FIG. 2 is a schematic representation of the motor module of FIG. 1 showing a plurality of motors forming part of the motor module.

FIG. 2 shows the underside of the motor module 2 with the outer casing 46 removed to reveal an inner casing 47. The motor module 2 comprises five primary motors 4, a secondary motor 6 and a translation motor 8, each mounted to the inner casing 47. Three of the primary motors 4 are positioned at locations B, C and D and are associated with the antagonistic rack and pinion mechanisms 10 shown in FIG. 1. The remaining two of the primary motors 4 are positioned at locations A and E and are associated with the dual antagonistic rack and pinion mechanisms 20 shown in FIG. 1.

The translation motor 8 is positioned at location F and is associated with the translation pinion 36.

The secondary motor 6 is positioned at location G and is associated with the secondary rack and pinion mechanism 30.

Referring back to FIG. 1, there is also a location F' positioned on the opposite side of the motor module 2 to location F. The translation motor 8 may be positioned at location F' rather than location F and the translation pinion 36 may accordingly be positioned on the opposite side of the motor module 2 to where it is situated in FIG. 1. The possibility of positioning and actuating the translation pinion 36 on either side of the motor module 2 allows two motor modules 2 to be configured so that they are symmetrical to one another.

Figure 3:
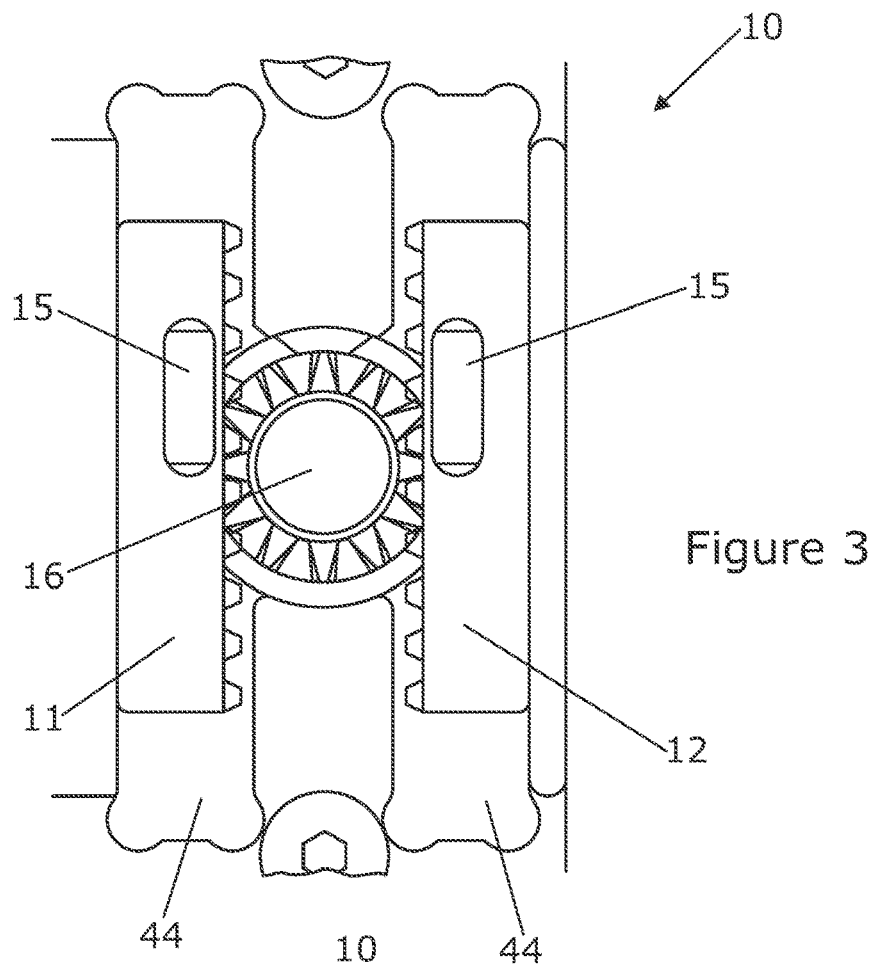
FIG. 3 is a schematic representation of an antagonistic rack and pinion mechanism forming part of the motor module of FIG. 1.

FIG. 3 shows one of the antagonistic rack and pinion mechanism 10 forming part of the motor module 2 shown in FIG. 1. The first and second primary racks 11, 12 are each moveably engageable with the primary pinion 16 wherein rotation of the primary pinion 16 causes movement of the first primary rack 11 in a first direction, and movement of the second primary rack 12 in a second direction. For example, clockwise rotation of the primary pinion 16 would cause the first primary rack 11 to move upwards and the second primary rack 12 to move downwards. Meanwhile, anticlockwise rotation of the primary pinion 16 would cause the first and second primary racks 11, 12 to move in the opposite directions (downwards and upwards respectively).

When used to actuate a surgical instrument, the antagonistic movement of the first and second primary racks 11, 12 may facilitate actuation of a pair of antagonistic tendons forming part of the surgical instrument. For example, in order to actuate a joint of the surgical instrument in a first direction a first tendon may be actuated (pulled), and to actuate the joint in a second direction, a second, antagonistic, tendon may be actuated (pulled). The antagonistic rack and pinion mechanism 10 may actuate the first tendon through rotation of the primary pinion 16 in a first direction, and the second tendon through rotation of the primary pinion 16 in a second, opposite, direction.

Each of the first and second primary racks 11, 12 comprises an actuation portion 15 and is movable linearly within a linear channel 44 forming part of the motor module 2.

Each linear channel 44 may restrict the positioning of the associated first or second primary rack 11, 12 so that it remains in contact with and tangential to the associated primary pinion 16. Further the linear channel 44 may restrict the movement of the associated first or second primary rack 11, 12 so that it may move only linearly between a first end and a second end of the linear channel 44.

The linear channels 44 may be configured within the motor module 2 so that, when the motor module 2 is in use with a surgical instrument, the linear channels 44 are parallel to the axis of the surgical instrument shaft. Therefore the linear movement of the primary racks 11, 12 and particularly the actuation portions 15 may be parallel to the required movement of the tendons of the surgical instrument. This obviates the need to significantly alter the direction of the tendons as they exit the shaft with Bowden cables or pulleys in order to be actuated by the actuation portions forming part of the antagonistic rack and pinion mechanisms 10 of the motor module 2.

Figure 4:
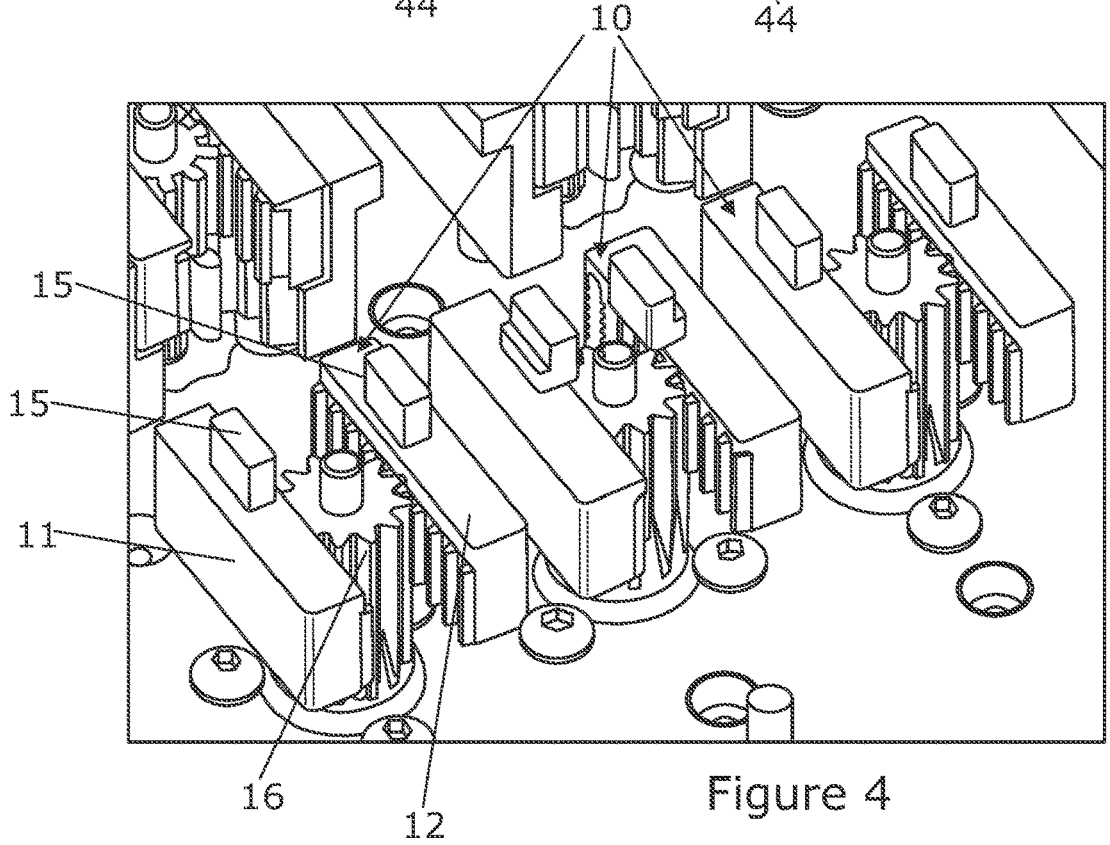
FIG. 4 is a schematic representation of a plurality of antagonistic rack and pinion mechanisms forming part of the motor module of FIG. 1.

FIG. 4 shows an all three antagonistic rack and pinion mechanisms 10 forming part of the motor module 2 shown in FIG. 1. In this embodiment of the invention, the primary pinion 16 comprises a plurality of teeth extending from its circumference and the first and second primary racks 11, 12 each comprise a plurality of teeth extending from a side of the primary rack 11, 12 proximate to the primary pinion 16. The teeth of the primary pinion 16 are adapted to interlock with the teeth of each primary rack 11, 12. When, in use, the primary pinion 16 is caused to rotate by the primary motor 4 (shown in FIG. 2), angular movement of the primary pinion's teeth may produce a force on the teeth of the primary rack and thereby cause the primary rack 11, 12 to move translationally relative to the primary pinion 16.

In other embodiments of the invention the first and second primary racks 11, 12 may be moveably engageable with the primary pinion 16 by any suitable means.

Figure 5:
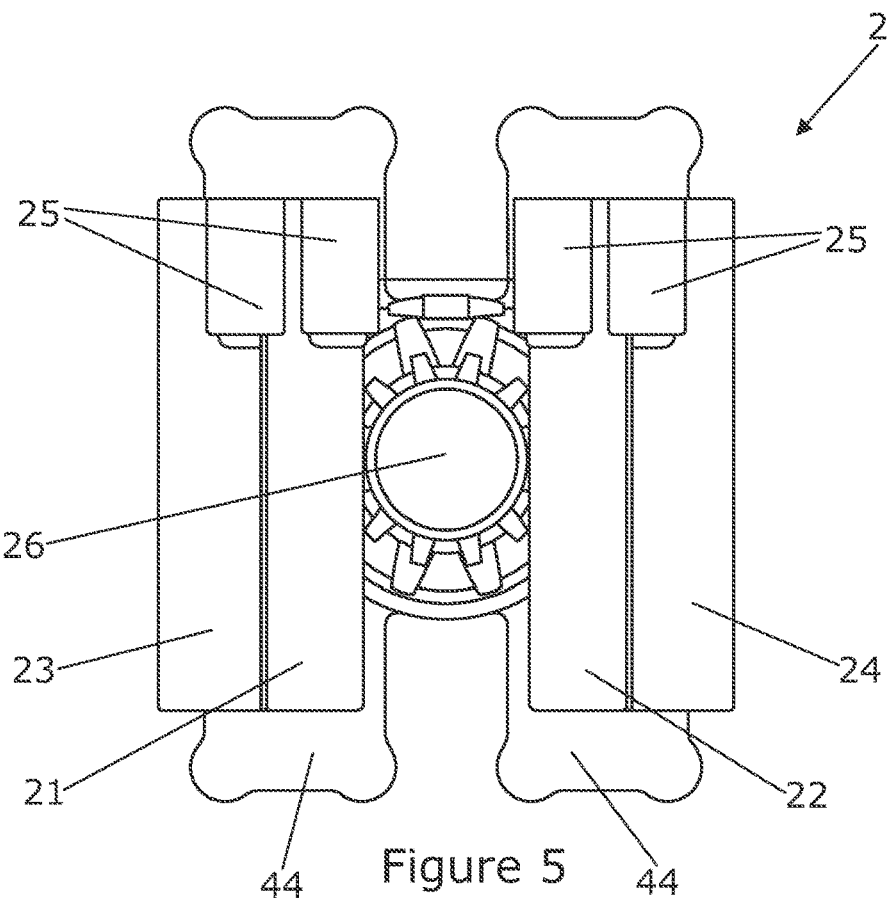
FIG. 5 is a schematic representation of a dual antagonistic rack and pinion mechanism forming part of the motor module of FIG. 1.

FIG. 5 shows one of the dual antagonistic rack and pinion mechanism 20 forming part of the motor module 2 shown in FIG. 1. The first, second, third and fourth primary racks 21, 22, 23 and 24 are each moveably engageable with the primary pinion 26 wherein rotation of the primary pinion 26 causes simultaneous movement of the first and third primary racks 21, 23 in a first direction, and movement of the second and fourth primary racks 22, 24 in a second direction. For example, clockwise rotation of the primary pinion 26 would cause the first and third primary racks 21, 23 to move upwards and the second and fourth primary racks 22, 24 to move downwards.

The dual antagonistic rack and pinion mechanism 20 therefore provides two pairs of antagonistically moveable primary racks (the first antagonistic pair being the first and second primary racks 21, 22 and the second antagonistic pair being the third and fourth primary racks 23, 24).

Figure 16:
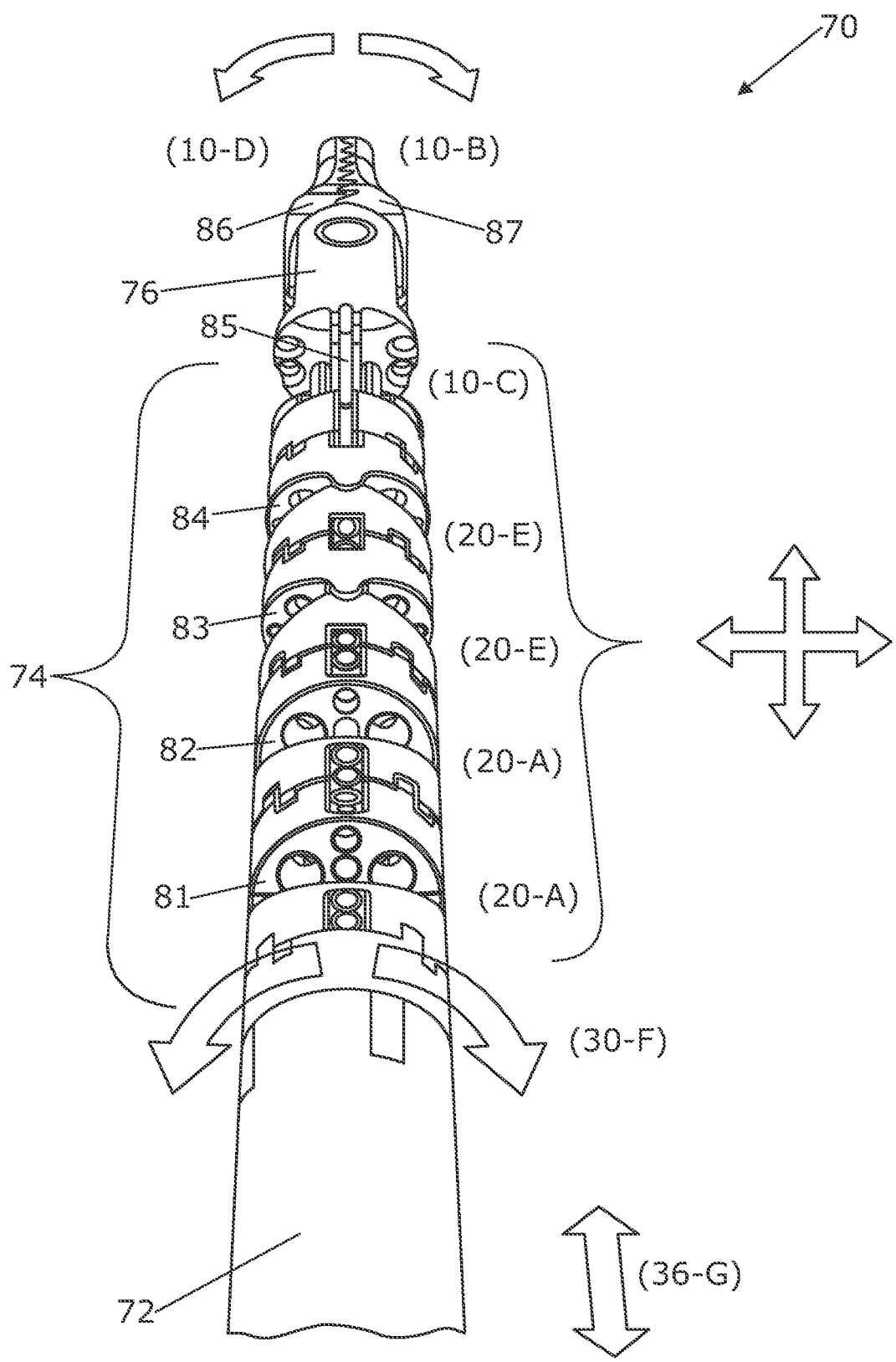
FIG. 16 is a schematic representation of the surgical instrument of FIGS. 13a, 13b and 13c.

This may be particularly advantageous for providing actuation of a surgical instrument comprising two adjacent joints that are rotatable in the same directions (see FIG. 16 for examples of adjacent joints). The dual antagonistic rack and pinion mechanism 20 may provide simultaneous actuation of the antagonistic pair of tendons associated with each of the adjacent joints. In other words, the dual antagonistic rack and pinion mechanism 20 may be used to actuate both adjacent joints simultaneously. This allows the two adjacent joints to actuate complimentarily with one another. Further, the actuation of both joints may be driven by a single primary motor 4 only, thereby reducing the complexity, size and cost of the motor module 2.

Each of the first, second, third and fourth primary racks 21, 22, 23, 24 comprises an actuation portion 25 and is movable linearly within a linear channel 44 similarly to the first and second primary racks forming part of the antagonistic rack and pinion mechanism shown in FIG. 3.

Each linear channel 44 may restrict the positioning of the associated first and third primary racks 21, 23 or second and fourth primary racks 22, 24 so that they both remain in contact with and tangential to the associated primary pinion 26. Further the linear channel 44 may restrict the movement of the associated first and third primary racks 21, 23 or second and fourth primary racks 22, 24 so that they are both able to moves only linearly between a first end and a second end of the linear channel 44.

As with the linear channels 44 associated with the antagonistic rack and pinion mechanisms 10, the linear channels 44 associated with the dual antagonistic rack and pinion mechanisms 20 may be configured within the motor module 2 so that, when the motor module 2 is in use with a surgical instrument, the linear channels 44 are parallel to the axis of the surgical instrument shaft. Therefore the linear movement of the primary racks 21, 22, 23, 24 and particularly the actuation portions 25 may be parallel to the required movement of the tendons of the surgical instrument.

Figure 6:
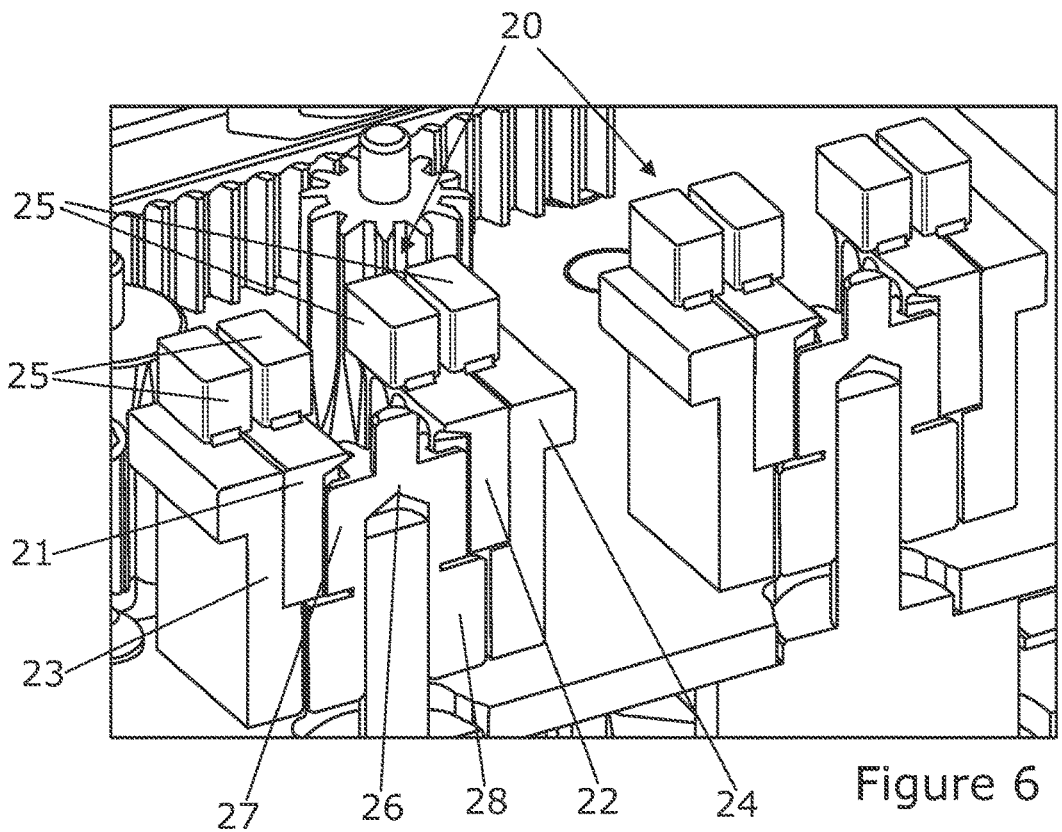
FIG. 6 is a schematic representation of a plurality of dual antagonistic rack and pinion mechanisms forming part of the motor module of FIG. 1.

FIG. 6 shows both dual antagonistic rack and pinion mechanisms 20 forming part of the motor module 2 shown in FIG. 1. In this embodiment of the invention the primary pinion 26 comprises a first portion 27 and a second portion 28 wherein the first and second primary racks 21, 22 are engageable with the first portion 27 and the third and fourth primary racks 23, 24 are engageable with the second portion 28.

Further, the first and second portions 27, 28 have different radii and may thereby cause the first and second primary racks 21, 22 to move with a different gearing ratio to the third and fourth primary racks 23, 24. In this embodiment of the invention, the second portion 28 has a larger radius than the first portion 27 so that, in use, rotation of the primary pinion 26 causes the third and fourth primary racks 23, 24 to move a greater distance than the first and second primary racks 21, 22 in their respective directions.

The radii of the first and second portions 27, 28 may be configured to ensure that, if the motor module 2 is used to actuate a surgical instrument with two adjacent joints, both joints may be actuated to rotate through the same angle of rotation despite a larger tendon actuation being required for the more distal of the two joints. For example, in this embodiment of the invention, the third and fourth primary racks 23, 24 may be configured to actuate the pair of antagonistic tendons associated with the more distal of the adjacent joints forming part of the surgical instrument as they will provide a larger actuation relative to the actuation provided by the first and second primary racks 21, 22.

FIGS. 7 and 8 show the secondary rack and pinion mechanism 30 forming part of the motor module 2 shown in FIG. 1. The secondary rack 32 is moveably engageable with the secondary pinion 34 wherein rotation of the secondary pinion 34 causes movement of the secondary rack 32. For example, in this embodiment of the invention, clockwise rotation of the secondary pinion 34 would cause the secondary rack 32 to move right, whereas anticlockwise rotation would cause the secondary rack 32 to move left.

The secondary rack 32 comprises an actuation portion 35 through which the secondary rack and pinion mechanism 30 may actuate an aspect of a surgical instrument. In this embodiment of the invention the secondary rack and pinion mechanism 30 is configured to provide a translational movement perpendicular to the movements provided by the primary rack and pinion mechanisms 10, 20. The 'side-to-side' movement of the secondary rack 32 may, for example, provide rotation of the shaft of the surgical instrument about its axis.

Referring particularly to FIG. 7, the secondary rack 32 is movable within a linear channel 44 similar to the linear channels 44 associated with the antagonistic and dual antagonistic rack and pinion mechanisms 10, 20. The linear channel 44 may restrict the positioning of the secondary rack 32 so that it remains in contact with and tangential to the associated secondary pinion 34. Further the linear channel 44 may restrict the movement of the secondary rack 32 so that it may move only linearly between a first end and a second end of the linear channel 44.

FIGS. 9 and 10 show the translational pinion 36 forming part of the motor module 2 shown in FIG. 1.

Referring particularly to FIG. 9, the translation pinion 36 is positioned to extend at least partially from the motor module 2 in order that it may interact with a translation rack (described in further detail with reference to FIG. 13). In order that the translation pinion 36 may be positioned close to the edge of the motor module while still being driven by the translation motor 8 positioned at location F, this embodiment of the invention further comprises a gear arrangement 37 (shown in FIG. 10) adapted to provide rotation of the translational pinion 36 about a different axis to the translational motor (location F).

Figure 11:
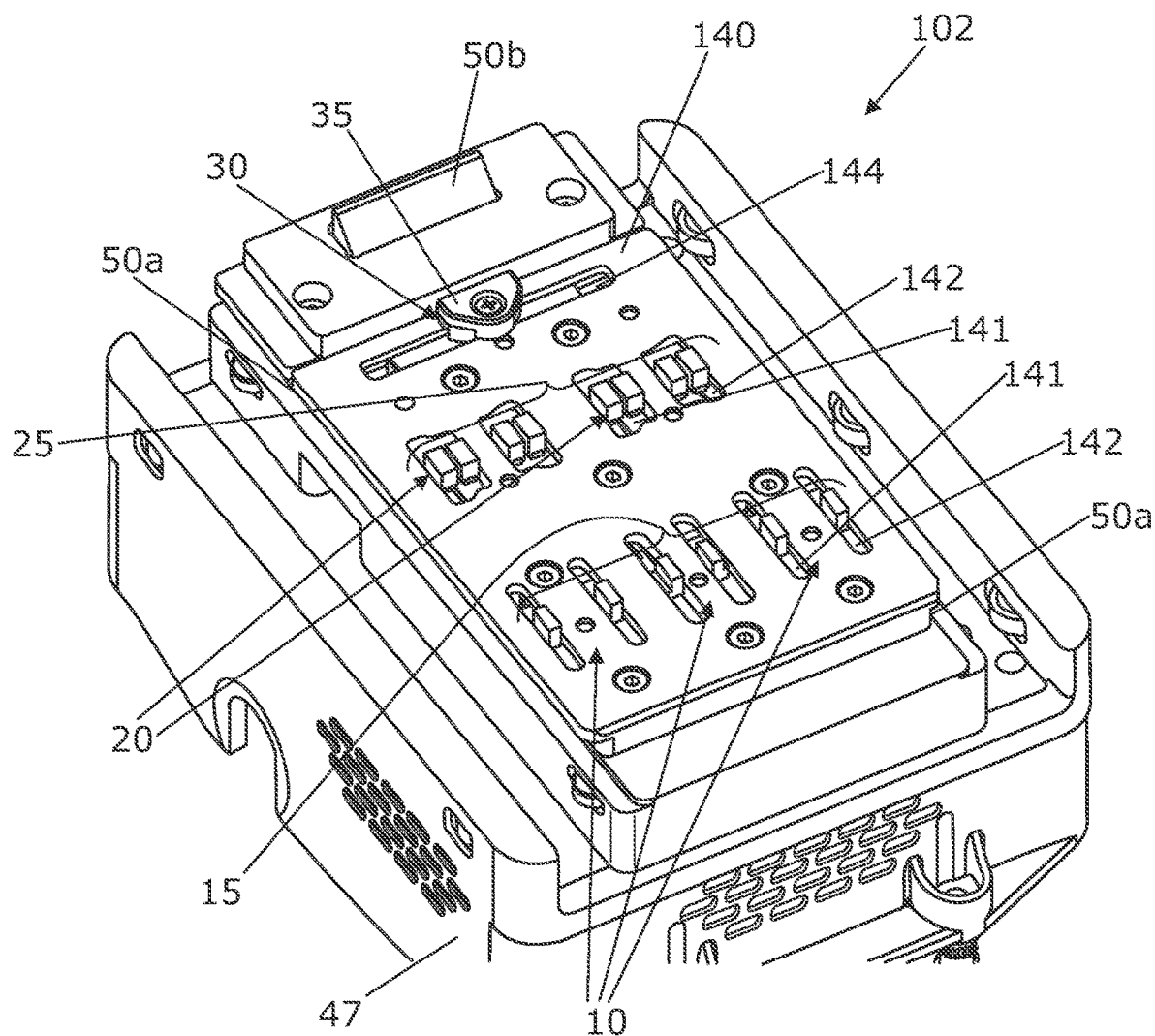
FIGS. 11 and 12 are schematic representations of a motor module, according to another embodiment of the invention, comprising an interface plate.
Figure 12:
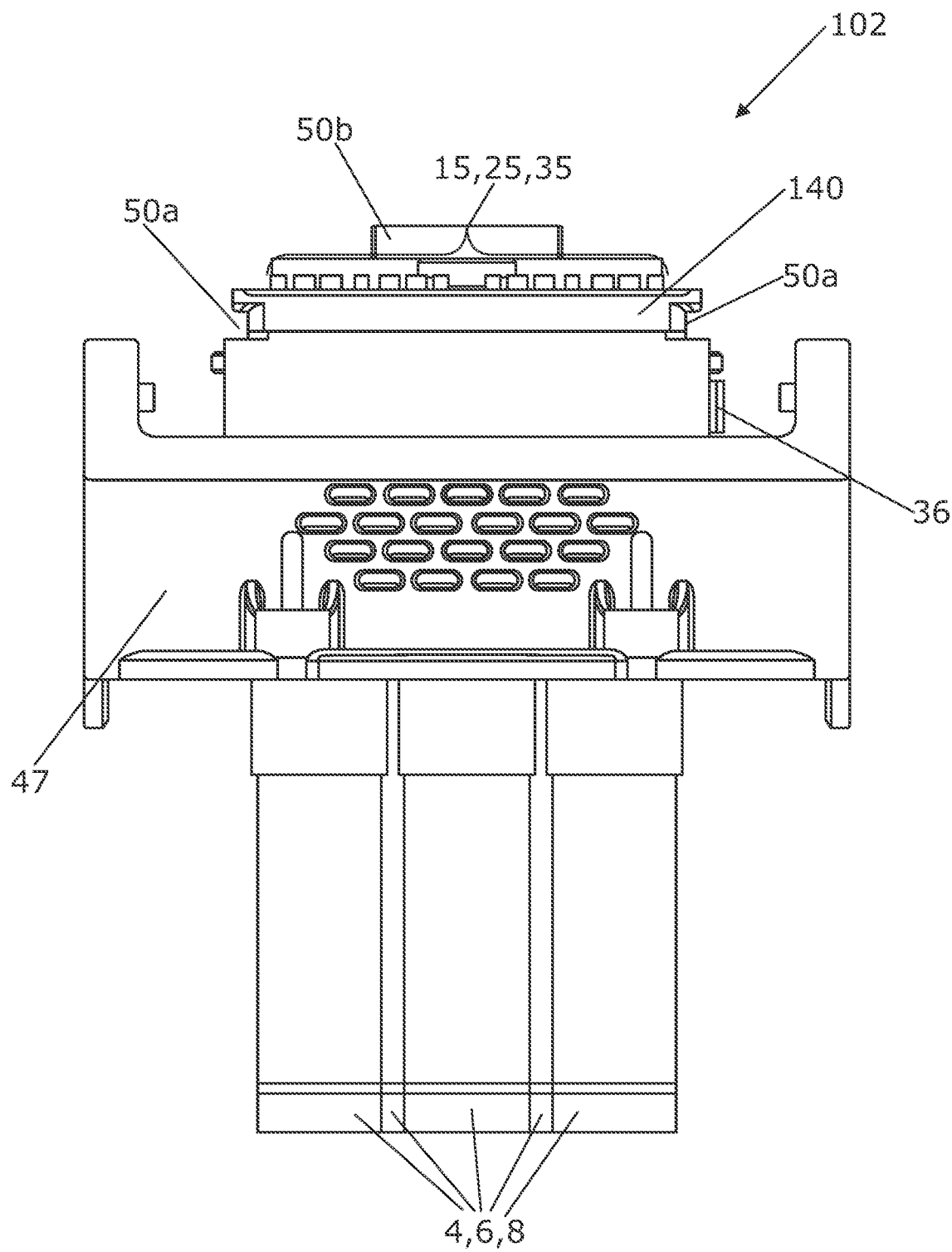

FIGS. 11 and 12 show a motor module 102 which is similar to the motor module 2 shown in FIG. 1 except that it further comprises an interface plate 140 and an instrument mount. In this embodiment of the invention, the instrument mount comprises a pair of channels 50a which facilitate slideable engagement of a surgical instrument via a sterile barrier and a latch 50*b* that facilitates lockable engagement of a surgical instrument via sterile barrier. (Similarly to FIG. 2 the outer casing 46 has been removed to reveal the inner casing 47 and motors 4, 6, 8.)

Referring particularly to FIG. 11, the interface plate 140 comprises a plurality of first apertures 141 and a plurality of second apertures 142. The actuation portion 15, 25 of each first primary rack 11, or each first and third primary rack 21, 23, is moveable within a respective one of the first apertures 141. Similarly, the actuation portion 15, 25 of each second primary rack 12, or of each second and fourth primary rack 22, 24, is moveable within a respective one of the second apertures 142. Also, the actuation portion 35 forming part of the secondary rack 32 is moveable within a secondary aperture 144.

The interface plate 140 covers and protects internal components of the motor module 102, such as the motors 4, 6, 8 (shown in FIG. 2) and pinions 16, 26, 34, 36 (shown in FIG. 1).

Referring now to FIG. 12 a translational pinion 36 (similar to the translational pinion shown in FIGS. 1, 9 and 10) extends from the motor module 2 such that it may engage with a translational rack forming part of a mounting bracket.

Figure 13A:
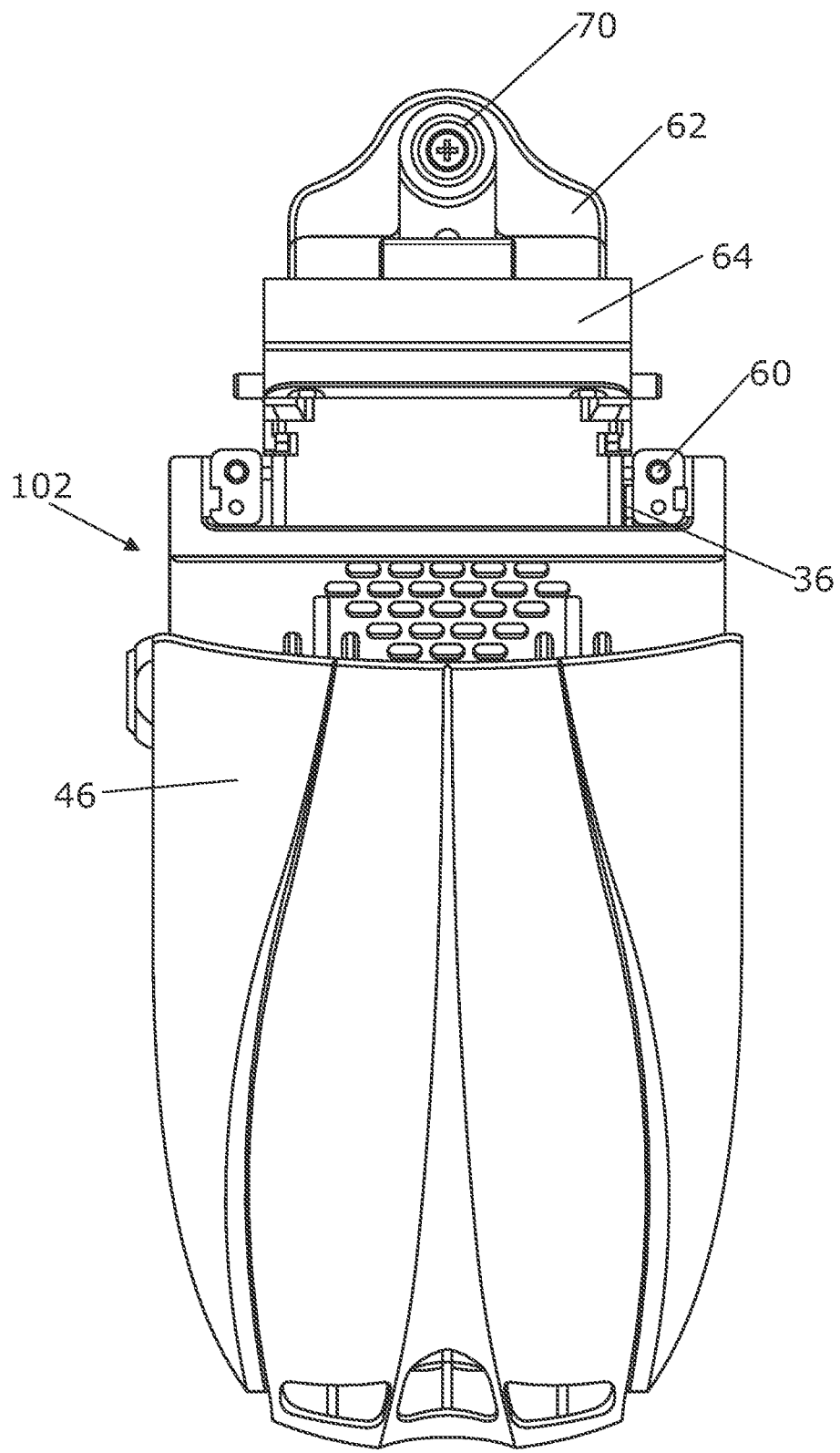
FIGS. 13a, 13b and 13c are schematic representations of the motor module of FIGS. 11 and 12 together with a mounting bracket, a sterile barrier, a driver module and a surgical instrument.
Figure 13B:
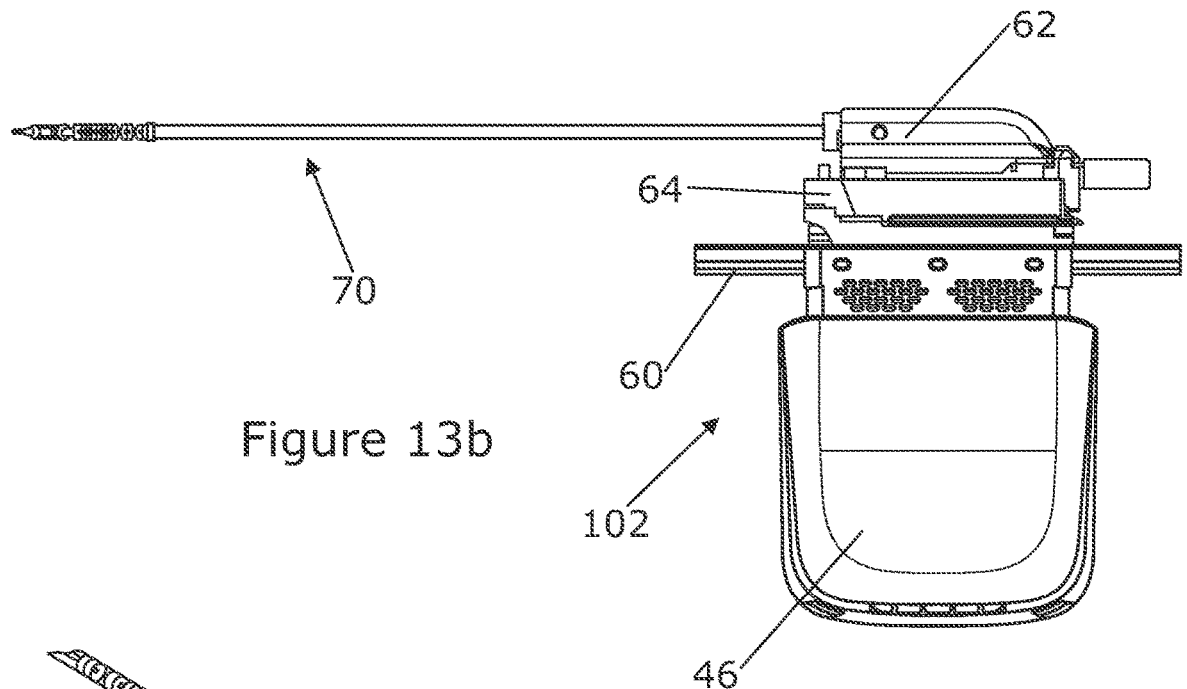
Figure 13C:
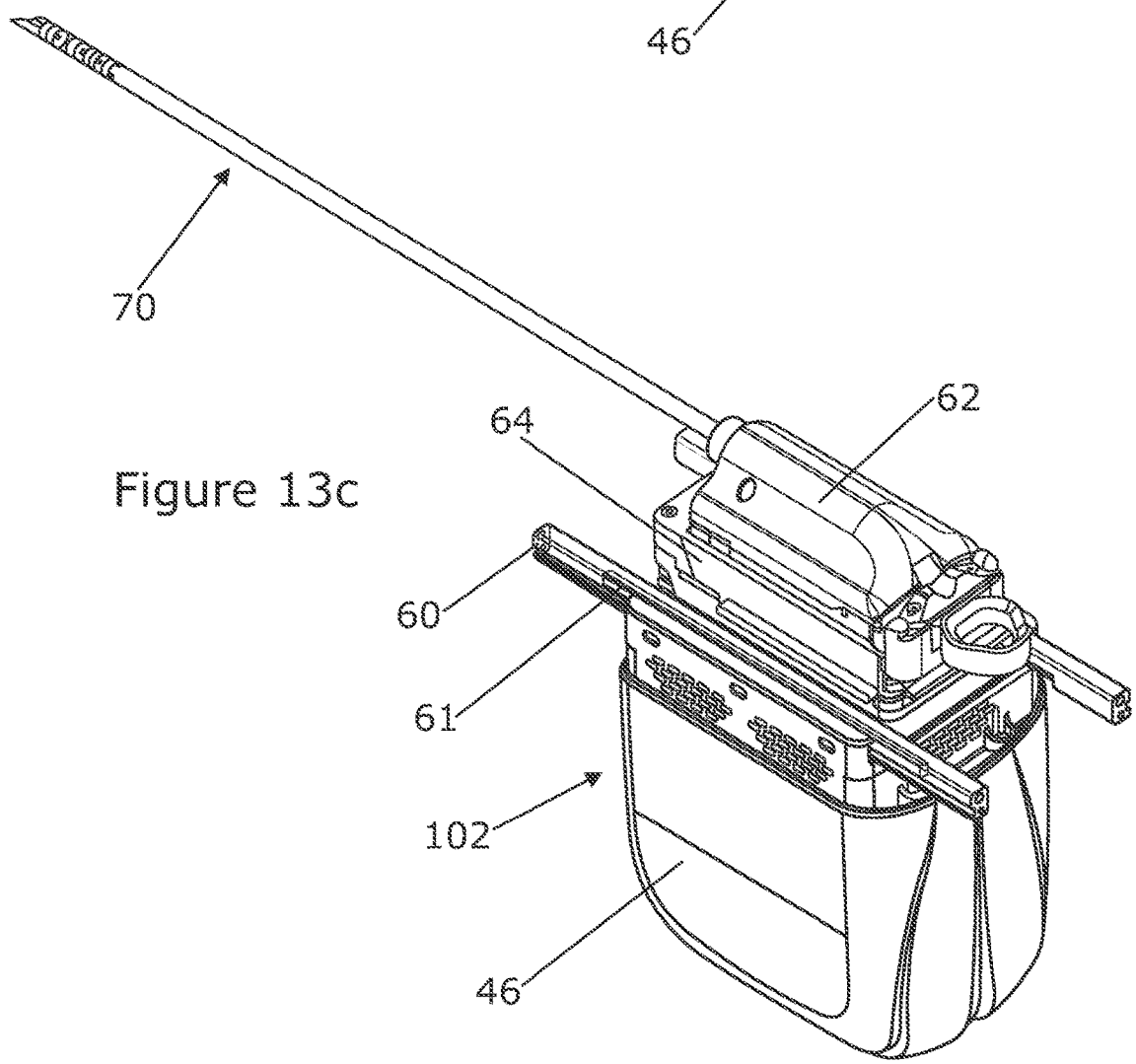

FIGS. 13*a*, 13*b* and 13*c* show the motor module 102 with the outer casing 46 covering the motors 4, 6, 8. The motor module 102 is removably mounted to a mounting bracket 60 such that the translational pinion 36 (shown more clearly in FIG. 12) is engaged with a translation rack 61 (shown particularly in FIG. 13*c*) forming part of the mounting bracket 60.

The gear arrangement 37 (shown in FIG. 10) may be adapted to provide gearing of the translation pinion's rotation relative to the rotation generated by the translational motor 8 (shown in FIG. 2). For example, the translation pinion 36 could be geared to rotate with a greater angular velocity than the translational motor 8 (shown in FIG. 2) to provide the resulting translation of the motor module 102 along the mounting bracket 60 with greater responsiveness relative to the input provided by the motor 8. Alternatively, the translation pinion 36 could be geared to rotate with a lower angular velocity than the translational motor 8 to provide the translational movements that may be achieved by motor module 102 relative to the mounting bracket 60 with greater precision.

FIGS. 13*a*, 13*b* and 13*c* also show a surgical instrument 70 extending from a driver module 62 which is removably mounted to a sterile barrier 64 which is, in turn, removably mounted to the motor module 102.

The sterile barrier 64 may comprise a slideable engagement feature that is engageable with the pair of channels 50*a* (shown in FIGS. 11 and 12), such as a complimentarily configured channels, ridges or grooves, and a lockable engagement feature that is engageable with the latch 50*b* (shown in FIGS. 11 and 12), such as a recess configured to receive the latch 50*b*. In use, the sterile barrier 64 may be slidably mounted to the motor module 102 by sliding the sterile barrier 64 over the interface plate 140 such that it engages with the channels 50*a* until the latch recess of the sterile barrier 64 is aligned with the latch 50*b* allowing the motor module 102 to lockably engage with the sterile barrier.

The driver module 62 may be mounted to the sterile barrier 64 in a similar fashion, or by any suitable means, such that the surgical instrument associated with the driver module is indirectly removably mounted to the motor module 102.

Figure 14:
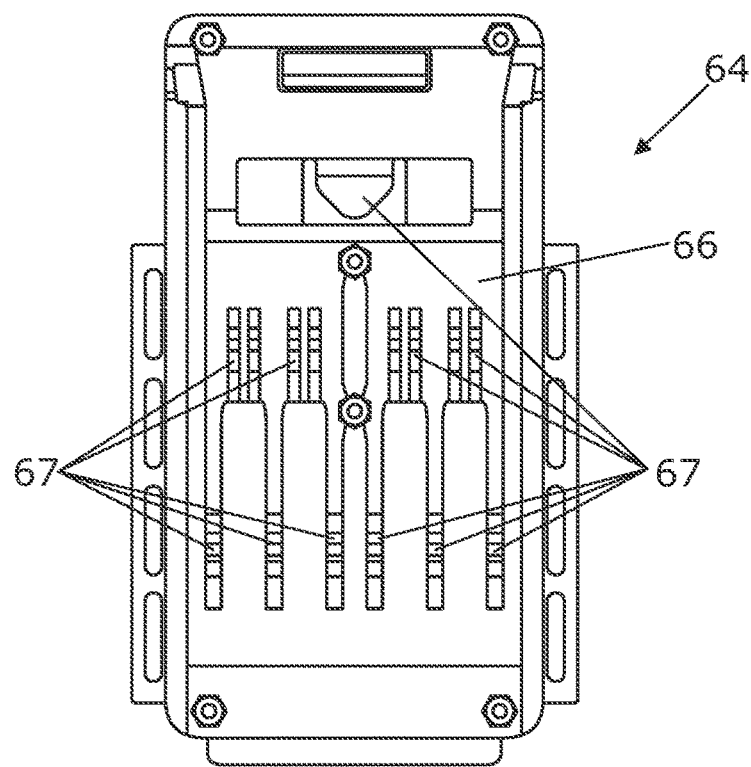
FIGS. 14 and 15 are schematic representations of first and second sides of the sterile barrier of FIGS. 13a, 13b and 13c.
Figure 15:
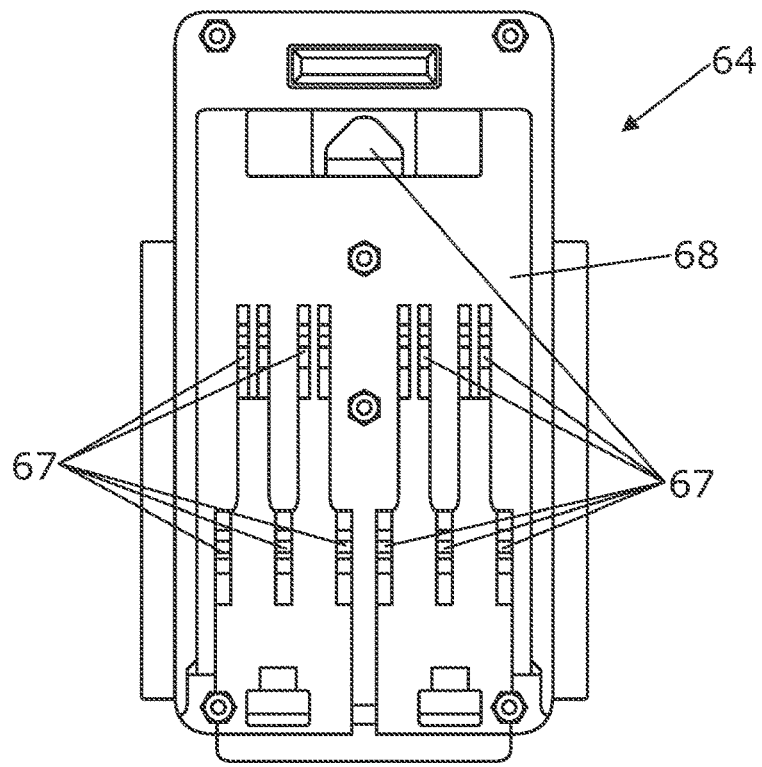

FIG. 14 shows a first side 66 of the sterile barrier 64 which may be removably mounted to motor module 102 and FIG. 15 shows a second side 68 of the sterile barrier 64 to which the driver module 62 may be mounted. The sterile barrier 64 comprises a plurality of movable translators 67.

In order for the motor module 102 to actuate the surgical instrument, the actuation portions 15, 25 and 35 (shown in FIG. 11) may engage with translators 67 via the first side of the sterile barrier 66. The translators 67 extend through the sterile barrier 64 such that they may engage with actuators forming part of the driver module 62 via the second side 68. Movement of the actuation portions 15, 25 and 35 of the motor module 102 may cause corresponding movement of the translators 67 which in turn may cause movement of the actuators of the driver module 62. Movement of the driver module actuators may cause actuation of the surgical instrument, possibly via tendons.

FIG. 16 shows the surgical instrument 70 which extends from the driver module 62 (as shown in FIGS. 13*a*, 13*b* and 13*c*). The surgical instrument 70 comprises a shaft 72 which may extend from the driver module 62, an articulation portion 74 coupled to the shaft 72 and an end effector 76 coupled to the articulation portion 74.

The surgical instrument 70 is capable of a plurality of actuations listed below:
translation of the surgical instrument 70 forwards or backwards,
rotation of the surgical instrument 70 clockwise or anti-clockwise,
actuation of a first pitch joints 81 and a second pitch joint 82 up or down,
actuation of a first yaw joint 83 and a second yaw joint 84 left or right,
actuation of a wrist joint 85 up or down,
actuation of a left jaw 86 clockwise or anticlockwise,
actuation of a right jaw 87 clockwise or anticlockwise,
actuation of jaws 86 and 87 in the same direction with same velocity results in a joint-like movement, and
actuation of jaws 86 and 87 in opposite directions results in the jaw opening/closing.

With reference to the corresponding features shown in FIGS. 1 to 13, each of the actuations listed above may be caused by the motor module 2 or 102 accordingly:

Translation Pinion 36

The translational motor 8 positioned at location F may rotate the translational pinion 36 clockwise or anticlockwise such that it rolls along the translational rack forming part of the mounting bracket 60. The motor module 2/102 (and surgical instrument 70 mounted to it) may thereby translate backwards and forwards relative to the mounting bracket 60.

Secondary Rack and Pinion Mechanism 30

The secondary motor 6 positioned at location G may rotate the secondary pinion 34 clockwise or anticlockwise to cause the secondary rack 32 to translate left or right. Resulting movement of the actuation portion 35 may be converted within the driver module to provide rotation of the surgical instrument 70 clockwise or anticlockwise.

Dual Antagonistic Rack and Pinion Mechanisms 20

The primary motor 4 positioned at location A may rotate the primary pinion 26 of the corresponding dual antagonistic rack and pinion mechanism 20 clockwise to cause the corresponding second and fourth primary racks 22, 24 to move away from the surgical instrument 70 (where the surgical instrument is positioned at the top of FIG. 1). Such a movement of the second and fourth primary racks 22, 24 may pull tendons associated with the pitch joints 81, 82 to cause them to actuate upwards. Conversely, anticlockwise rotation of the primary pinion 26 may cause the corresponding first and third primary racks 21, 23 to move away from the surgical instrument 70 and thereby pull tendons also associated with the pitch joints 81, 82 to cause them to actuate downwards.

Similarly, the primary motor 4 positioned at location E may rotate the primary pinon 26 of the corresponding dual antagonistic rack and pinion mechanism 20 clockwise or anticlockwise to cause the yaw joints 83, 84 to actuate right or left respectively.

Antagonistic Rack and Pinion Mechanisms 10

The primary motor 4 positioned at the location C may rotate the primary pinion 16 of the corresponding antagonistic rack and pinon mechanism 10 clockwise to cause the corresponding second primary rack 12 move away from the surgical instrument 70. Such a movement of the second primary rack may pull a tendon associated with the wrist joint 85 to cause it to actuate upwards. Conversely, anticlockwise rotation of the primary pinion 16 may cause the corresponding first primary rack 11 to move away from the surgical instrument 70 and thereby pull the other of the antagonistic tendons associated with the wrist joint 85 to cause the wrist joint 85 to actuate downwards.

Similarly, the primary motors 4 position at locations D and B may each rotate the primary pinion 16 of the corresponding antagonistic rack and pinion mechanism clockwise or anticlockwise in order to pull a tendon associated with the left jaw 86 and right jaw 87 respectively. In each case, clockwise rotation of the primary pinion 16 causes clockwise actuation of the relevant jaw 86, 87 and anticlockwise rotation of the primary pinion 16 causes anticlockwise actuation of the relevant jaw 86, 87.

The surgical instrument 70 is an example of a surgical instrument that may be actuated with a motor module according to an embodiment of the invention. A motor module according to an embodiment of the invention may be used to actuate any suitable surgical instrument. For example, the shaft may be longer or shorter than the shaft 72 shown, the articulation portion may comprise more or fewer joints than the articulation portion 74 shown and the end effector may be different to the end effector 76 shown. The end effector may be a scalpel, scissors, a caterising tool, a suction tool or an injection needle for example.

Figure 17:
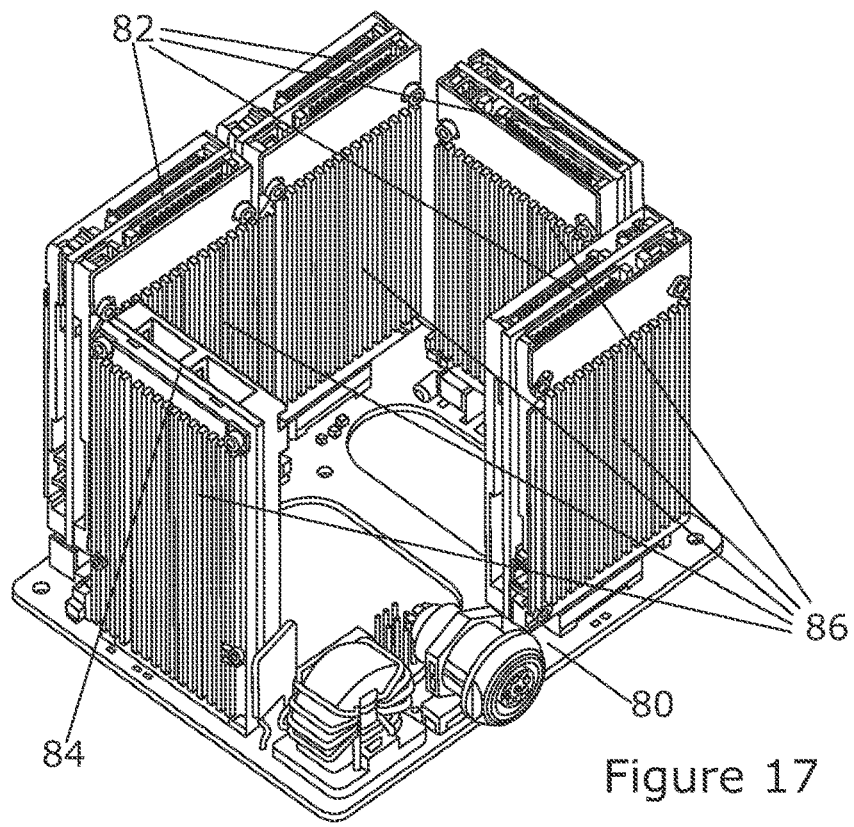
FIGS. 17 and 18 are schematic representations of internal components forming part of the motor modules shown in FIG. 1 and FIGS. 11 and 12.

Referring now to FIG. 17 internal components of a motor module 2, 102 are shown. The internal components include four processors 82 and a safety watchdog 84, each mounted to a motherboard 80. The safety watchdog 84 may be electrically connectable to each processor 82 via the motherboard 80.

Each processor 82 may receive control signals from a control module forming part of the robotic surgical system. Based on the control signals each processor 82 may selectively provide electrical power to one or more of the motors 4, 6, 8 forming part of the motor module 2, 102 in order to cause the motor to provide a rotational movement.

The safety watchdog 84 may monitor the motor module 2, 102 for errors such as a failed motor, a motor that is unable to complete its controlled movement (which may indicate a blockage within the system) or the processor failing to carry out a control signal.

Further, a heat sink 86 is mounted to each processor 82 and the safety watchdog 84. Each heat sink 86 may absorb heat produced by the processors 82 and the safety watchdog 84 during use of the motor module 2, 102. Each heat sink 86 comprises a cooling surface with fins that increase the surface area of the heat sink 86 and improve heat dissipation.

Each heat sink 86 may therefore help prevent components of the motor module 2, 102 from overheating.

Figure 18:
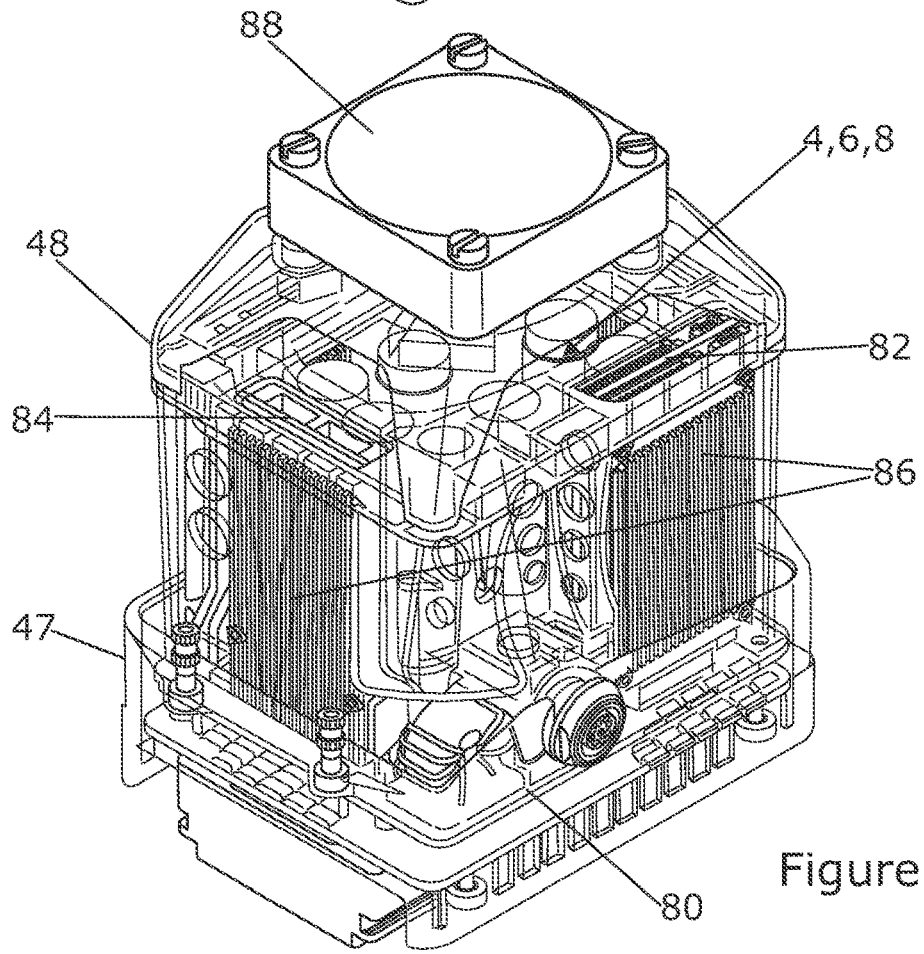

Referring now to FIG. 18, the motherboard 80 is mounted to the inner casing 47 of a motor module 2, 102 (shown in FIGS. 2 and 12) such that the processors 82 and safety watchdog 84 are positioned around the motors 4, 6, 8. A chassis 48 is also mounted to the inner casing 47, the chassis 48 being adapted to support the various internal components in their intended positions within the motor module 2, 102.

A cooling fan 88 is mounted to the chassis 48. The cooling fan may be operated to cause air to flow through the motor module 2, 102 and facilitate cooling of the internal components, particularly the motors 4, 6, 8, processors 82 and the heat sinks 86. Further, the cooling fan 88 is oriented to cause air to flow parallel to the motors 4, 6, 8, processors 82 and safety watchdog 84.

In addition, the fins of the heat sinks 86 extend parallel to the air flow caused by the cooling fan 88. This may encourage air to flow across the cooling surface of the heatsinks and improve the dissipation of heat from them, therefore further helping to prevent components of the motor module 2, 102 from over heating.

Preferences and options for a given aspect, feature or parameter of the invention should, unless the context indicates otherwise, be regarded as having been disclosed in combination with any and all preferences and options for all other aspects, features and parameters of the invention. For example, a motor module according to an embodiment of the invention may comprise more than one secondary rack and pinion mechanism or may comprise no secondary rack and pinion mechanisms rather than comprising only one secondary rack and pinion mechanism as is demonstrated in FIGS. 1 to 15.

The invention claimed is:

1. A motor module comprising:
a primary pinion rotatably driveable by a primary motor,
a first primary rack moveably engageable with the primary pinion and
a second primary rack moveably engageable with the primary pinion; wherein
rotation of the primary pinion causes movement of the first primary rack in a first direction, and movement of the second primary rack in a second direction, whereby the first and second primary racks and the primary pinion together form an antagonistic rack and pinion mechanism;
wherein the motor module comprises a plurality of motors and a plurality of antagonistic rack and pinion mechanisms, wherein the primary pinion of each antagonistic rack and pinion mechanism is driveable by a respective one of the motors;
wherein at least one of the antagonistic rack and pinion mechanisms is a dual antagonistic rack and pinion mechanism further comprising:
a third primary rack moveably engageable with the primary pinion and
a fourth primary rack moveably engageable with the primary pinion; wherein
rotation of the primary pinion causes movement of the third primary rack in the first direction and movement of the fourth primary rack in the second direction.

2. A motor module according to claim 1 wherein
the primary pinion of the or each dual antagonistic rack and pinion mechanism comprises a first portion and a second portion,
the first and second primary racks being engageable with the first portion of the primary pinion, and the third and fourth primary racks being engageable with the second portion of the primary pinion.

3. A motor module according to claim 1 wherein:

each primary rack further comprises an actuation portion, the motor module further comprises an interface plate comprising a plurality of first apertures and a plurality of second apertures, the actuation portion of each first primary rack, or each first and third primary rack, is moveable within a respective first aperture, and the actuation portion of each second primary rack, or each second and fourth primary rack, is moveable within a respective second aperture.

4. A motor module according to claim 1 wherein each primary rack is movable linearly.

5. A motor module according to claim 1 further comprising a secondary motor and a secondary rack and pinion mechanism, the secondary rack and pinion mechanism comprising:

a secondary pinion rotatably driveable by the secondary motor, a secondary rack movably engageable with the secondary pinion wherein rotation of the secondary pinion causes movement of the secondary rack.

6. A motor module according to claim 1 wherein the motor module is removably mountable to a mounting bracket and is movable along the mounting bracket.

7. A motor module according to claim 6 wherein the mounting bracket comprises a translation rack and the motor module further comprises a translation motor and a translation pinion rotatably driveable by the translation motor and engageable with the translation rack when the motor module is mounted to the mounting bracket such that rotation of the translation pinion causes movement of the motor module relative to the mounting bracket.

8. A motor module according to claim 7 further comprising a gear arrangement rotatably driveable by the translation motor and rotatably and mechanically coupled to the translation pinion such that the translation pinion is rotatably driven by the translation motor via the gear arrangement.

9. A motor module according to claim 1 wherein the motor module is configured to actuate a surgical instrument.

10. A motor module according to claim 9 further comprising an instrument mount mechanically couplable to a surgical instrument such that the surgical instrument is removably mountable to the motor module.

11. A motor module according to claim 1 further comprising a processor electrically connectable to at least one motor.

12. A motor module according to claim 11 further comprising a safety watchdog electrically connectable to the processor.

13. A motor module according to claim 1 further comprising a heat sink, a cooling fan or both.

* * * * *